United States Patent [19]

Fengler et al.

[11] Patent Number: 4,861,878
[45] Date of Patent: Aug. 29, 1989

[54] 1H-PYRIDO-(2,3-B) (1,4)-THIAZINES

[75] Inventors: Gerd Fengler; Alexander Klausener; Hans-Josef Buysch, all of Krefeld, Fed. Rep. of Germany; Mithat Mardin, Madison, Conn.; Bernhard Pelster, St. Augustin, Fed. Rep. of Germany

[73] Assignee: Bayer Aktiengesellschaft, Leverkusen, Fed. Rep. of Germany

[21] Appl. No.: 927,909

[22] Filed: Nov. 6, 1986

[30] Foreign Application Priority Data

Nov. 16, 1985 [DE] Fed. Rep. of Germany ....... 3540702

[51] Int. Cl.⁴ .......................................... C07D 513/04
[52] U.S. Cl. ......................................... 544/48; 544/34
[58] Field of Search ................................... 544/48, 34

[56] References Cited

U.S. PATENT DOCUMENTS 4,784,997 11/1988 Klausener et al. ................... 544/48

FOREIGN PATENT DOCUMENTS 0100527 2/1984 European Pat. Off. ............ 514/225
0101898 3/1984 European Pat. Off. ............ 514/225

OTHER PUBLICATIONS

Beilstens Handbuch der Organischen Chemie, Band 27, Teil 11, 3. und 4. Erganzungswerk, 4. Auflage, Springer-Verlag, 1984, Berlin, DE *Seite 7916, Verbindung der Formel VII; Seite 7956, Verbindung der Formel VI*.
Chemical Abstracts, Band 83, Nr. 23, 8. Dezember 1975, Seite 476, Spalte 2, Zusammenfassungs Nr. 193384y; & SU- A - 430 642 (Ordzhonikidze, S., All-Union Scientific-Research Chemical-Pharmaceutical Institute).
Safonova et al, CA, vol. 83, 83: 193384y, p. 476, 1975.
Safonova et al, CA, vol. 74, 1971, 74: 141668p.
Shen et al, "The Development of Antiasthma Drug", Part III, ed. D. R. Buckle et al, Butterworth Publishers, Kent, England, 1980, pp. 315-317; 331-335.

*Primary Examiner*—John M. Ford
*Attorney, Agent, or Firm*—Sprung Horn Kramer & Woods

[57] ABSTRACT

New potent lipoxygenase inhibitors which are 1H-pyrido-[2,3-b][1,4] thiazines are disclosed. The new thiazines are of the formula

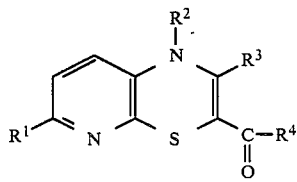

in which $R^1$ denotes hydrogen, halogen, optionally substituted alkyl or alkoxy or the group

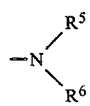

in which $R^5$ and $R^6$ are identical or different and denote hydrogen, optionally substituted alkyl or aryl, or can be linked to form a 5- or 6-membered heterocyclic ring,
$R^2$ and $R^3$ are identical or different and denote hydrogen or optionally substituted alkyl or alkoxy and
$R^4$ denotes hydroxyl, the group

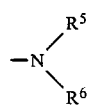

in which $R^5$ and $R^6$ have the abovementioned meaning, or, in the case where $R^3$ denotes hydrogen or optionally substituted alkoxy, also denotes optionally substituted alkoxy.

6 Claims, No Drawings

1H-PYRIDO-(2,3-B) (1,4)-THIAZINES

The present invention relates to a new 1H-pyrido-[2,3-b][1,4]-thiazines and quaternary salts thereof, processes for their preparation and their use in medicaments.

It is known that the metabolites of arachidonic acid formed by the enzyme lipoxygenase participate in the development of inflammatory and allergic processes (E.J. Goetzl, Immunology 40, 709 (1980); Ford-Hutchinson et al., J. Pharm. Pharmacol. 32, 517 (1980) and Nature 286, 264 (1980) and Samuelsson Trends in Pharmacol. Sci., 1980, 227; and Borgeat et al., J. Med. Chem. 24, 121 (1981)).

Pyrido-[2,3-b][1,4]-thiazines are known from C.A. 83, 193384 y (1975) and C.A. 74, 141668 p (1971).

The subject matter of the present invention relates to novel 1H-pyrido-[2,3-b][1,4]-thiazines of the formula

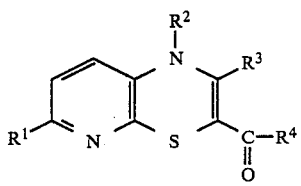 (I)

in which $R^1$ denotes hydrogen, halogen, optionally substituted alkyl or alkoxy or the group

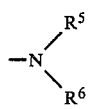

in which $R^5$ and $R^6$ are identical or different and denote hydrogen, optionally substituted alkyl or aryl, or can be linked to form a 5- or 6-membered heterocyclic ring, $R^2$ and $R^3$ are identical or different and denote hydrogen or optionally substitued alkyl or alkoxy and $R^4$ denotes hydroxyl, the group

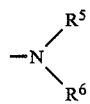

in which $R^5$ and $R^6$ have the abovementioned meaning, or, in the case where $R^3$ denotes hydrogen or optionally substituted alkoxy, also denotes optionally substituted alkoxy, wherein $R^3$ and $R^4$ can be linked via a polymethylene chain to form a 5- to 7-membered carbocyclic ring, and wherein, in the case of a 6-membered carbocylic ring, $R^1$ does not denote hydrogen, chlorine, methoxy or ethoxy, and quaternary salts thereof.

Surprisingly, the new 1H-pyrido-[2,3-b][1,4]-thiazines are potent lipoxygenase inhibitors. Quite unexpectedly they already inhibit lipoxygenase very specifically in concentrations at which cyclooxygenase is not influenced. This very potent and specific action of the 1H-pyrido[2,3-b][1,4]-thiazines was not to be expected.

Halogen, in general, represents fluorine, chlorine, bromine or iodine, preferably fluorine, chlorine or bromine.

Alkyl, in general, represents a straight-chain or branched hydrocarbon radical with 1 to 8 carbon atoms. Lower alkyl with 1 to about 6 carbon atoms is preferred. Examples which may be mentioned are methyl, ethyl, propyl, isopropyl, butyl, isobutyl, pentyl, isopentyl, hexyl and isohexyl.

Alkoxy, in general, represents a straight-chain or branched hydrocarbon radical which has 1 to 8 carbon atoms and is bonded via an oxygen atom. Lower alkoxy with 1 to about 6 carbon atoms is preferred. Examples which may be mentioned are methoxy, ethoxy, propoxy, isopropoxy, butoxy, isobutoxy, pentoxy, isopentoxy, hexoxy and isohexoxy.

Aryl, in general, represents an aromatic radical with 6 to about 12 carbon atoms. Preferred aryl radicals are phenyl, naphthyl and diphenyl.

The alkyl, alkoxy and aryl radicals can be substituted by active groups. For example, they can be substituted by halogen, preferably chlorine and bromine, hydroxyl, amino, dimethylamino, diethylamino, cyano, methoxycarbonyl or ethoxycarbonyl. The radicals can carry 1 to 3, preferably one, substituent.

The radicals $R_5$ and $R_6$ can be linked to form a 5- or 6-membered heterocyclic ring. Examples of these which may be mentioned are the following heterocyclic rings: pyrrolidine, pyrrole, imidazole, piperidine, piperazine, N-methylpiperazine and morpholine.

The radicals $R_3$ and $R_4$ can be linked via a polymethylene chain to form a 5- to 7-membered carbocyclic ring. The following carbocyclic rings may be mentioned as examples: cyclopentenone, cyclohexenone and cycloheptenone.

Preferred 1H-pyrido-{2,3-b][1,4]-thiazines of the formula (I) are those in which $R^1$ denotes hydrogen, halogen, alkoxy ($C_1$ to $C_8$) or alkyl ($C_1$ to $C_8$), optionally substituted by halogen, hydroxyl, amino, dimethylamino, diethylamino, cyano, methoxycarbonyl or ethoxycarbonyl, or the group

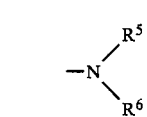

in which $R^5$ and $R^6$ are identical or different and denote hydrogen, or aryl ($C_6$ to $C_{12}$) or alkyl ($C_1$ to $C_8$), optionally substituted by halogen, hydroxyl, amino, dimethylamino, diethylamino, cyano, methoxycarbonyl or ethoxy-carbonyl or can be linked by a hydrocarbon chain to form a 5-or 6-membered heterocyclic ring, $R^2$ and $R^3$ are identical or different and denote hydrogen or alkoxy ($C_1$ to $C_8$) or alkyl ($C_1$ to $C_8$) optionally substituted by halogen, hydroxyl, amino, dimethylamino, diethylamino, cyano, methoxycarbonyl or ethoxycarbonyl, $R^4$ denotes hydroxyl or the group

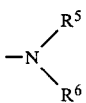

in which
R⁵ and R⁶ have the abovementioned meaning, or, in the case where R³ denotes hydrogen or optionally substituted alkoxy, also denotes $C_1$ to $C_8$ alkoxy or $C_1$ to $C_8$-alkoxy substituted by halogen, hydroxyl, amino, dimethylamino, diethylamino, cyano, methoxycarbonyl or ethoxycarbonyl wherein R³ and R⁴ can be linked via a polymethylene chain to form a 5- to 7-membered carbocyclic ring, and wherein, in the case of a 6-membered carbocylcic ring, $R_1$ does not denote hydrogen, chlorine, methoxy or ethoxy, and quaternary salts thereof.

Particularly preferred 1H-pyrido-[2,3-b][1,4]-thiazines of the formula (I) are those in which R¹ denotes hydrogen, fluorine, chlorine, bromine, lower alkoxy ($C_1$ to $C_6$) or lower alkyl ($C_1$ to $C_6$) optionally substituted by chlorine, bromine, hydroxyl, amino, dimethylamino, diethylamino, cyano, methoxycarbonyl or ethoxycarbonyl, or the group

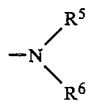

in which
R⁵ and R⁶ are identical or different and denote hydrogen, phenyl or lower alkyl($C_1$ to $C_6$), optionally substituted by chlorine, bromine, hydroxyl, amino, dimethylamino, diethylamino, cyano, methoxycarbonyl or ethoxycarbonyl, or can be linked to form a morpholine or piperazine ring, R² and R³ are identical or different and denote hydrogen or lower alkoxy ($C_1$ to $C_6$) or lower alkyl ($C_1$ to $C_6$), optionally substituted by chlorine, bromine, hydroxyl, amino, dimethylamino, diethylamino, cyano, methoxycarbonyl or ethoxycarbonyl, R⁴ denotes hydroxyl or the group

in which
R⁵ and R⁶ have the abovementioned meaning, or, in the case where R³ denotes hydrogen or lower alkoxy ($C_1$ to $C_6$), also denotes lower alkoxy ($C_1$ to $C_6$), substituted by chlorine, bromine, hydroxyl, amino, dimethylamino, diethylamino, cyano, methoxycarbonyl or ethoxycarbonyl, wherein R³ and R⁴ can be linked via a polymethylene chain to form a 5- to 7-membered carbocyclic ring, and wherein, in the case of a 6-membered carbocyclic ring, $R_1$ does not denote hydrogen, chlorine, methoxy or ethoxy, and quaternary salts thereof.

Quaternary salts of the 1H-pyrido-[2,3-b][1,4]-thiazines according to the invention are formed by reaction with compounds of formula (II)

$$R^7-X \qquad (II)$$

in which
R⁷ denotes alkyl and
X denotes a nucleofugic group, (a good leaving group).

The quaternary salts are preferably prepared by reaction with halides or tosylates of the formula (II)

$$R^7-Z \qquad (II)$$

in which
R⁷ denotes lower alkyl and
Z denotes halogen or 0-tosylate.

The following 1H-pyrido-[2,3-b][1,4]-thiazines and quaternary salts thereof may be mentioned as examples:

| R¹ | R² | R³ | R⁴ |
| --- | --- | --- | --- |
| H | H | H | OCH₃ |
| H | H | H | O—C₂H₅ |
| H | H | H | O—CH(CH₃)₂ |
| H | H | H | O—CH₂CH₂CH₂CH₃ |
| H | H | H | O—CH₂CH(CH₃)₂ |
| H | H | H | OC(CH₃)₃ |
| H | H | H | O—(CH₂)₄CH₃ |
| H | H | H | O—(CH₂)₅CH₃ |
| H | H | H |  |
| H | H | H |  |
| Cl | H | H | O(CH₂)₃CH₃ |
| Cl | H | H | O—CH₂—C₆H₅ |

-continued

| | | | |
|---|---|---|---|
| Cl | H | H | OCH₂CH₂–C₆H₅ |
| Cl | CH₂COOC₂H₅ | H | O(CH₂)₃CH₃ |
| N(CH₃)₂ | H | H | O(CH₂)₃CH₃ |
| N(C₂H₅)₂ | H | H | O–CH₂–C₆H₅ |
| piperidin-1-yl | H | H | OCH₂CH₂–C₆H₅ |
| morpholin-4-yl | H | H | OC₂H₅ |
| 4-methylpiperazin-1-yl | H | H | O(CH₂)₃CH₃ |
| H | H | H | NH₂ |
| H | H | H | NHC₂H₅ |
| H | H | H | NHC(CH₃)₃ |
| H | H | H | NH–C₆H₅ |
| H | H | H | NH—(CH₂)₂—OH |
| H | H | H | NH—(CH₂)₂—NH₂ |
| H | H | H | NH—(CH₂)₃—N(C₂H₅)₂ |
| H | H | H | N(C₂H₅)₂ |
| H | H | H | piperidin-1-yl |
| H | H | H | morpholin-4-yl |
| H | H | H | N(C₆H₅)(C₂H₅) |
| H | H | CH₃ | N(C₂H₅)₂ |
| H | H | C₂H₅ | NH—(CH₂)₃—N(C₂H₅)₂ |
| H | H | C₂H₅ | 4-methylpiperazin-1-yl |
| Cl | H | C₂H₅ | 4-methylpiperazin-1-yl |

-continued

| | | |
|---|---|---|
| N(C₂H₅) | H | H, —N(morpholino-O) |
| —N(morpholino-O) | CH₂CN | C₂H₅, —N(N-methylpiperazino)—CH₃ |
| H | H | R₃ or R₄ —CH₂—CH₂—CH₂—CH₂ |
| Cl | H | R₃ or R₄ —CH₂—CH₂—CH₂—CH₂ |
| H | H | R₃ or R₄ —CH₂—CH₂ |
| Cl | H | R₃ or R₄ —CH₂—CH₂ |
| N(C₂H₅)₂ | H | R₃ or R₄ —CH₂—CH₂ |

Salts

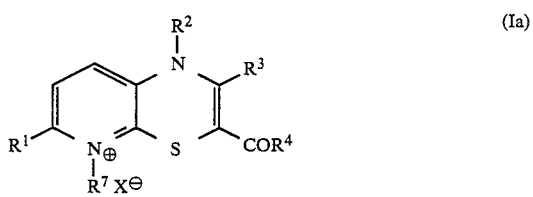
(Ia)

| R₁ | R₂ | R₃ | R₄ | R₇ | X |
|---|---|---|---|---|---|
| H | H | H | OC₂H₅ | CH₃ | I |
| H | H | H | OC₂H₅ | C₂H₅ | I |
| H | H | H | OC₂H₅ | CH₂COOC₂H₅ | Br |
| H | H | H | O(CH₂)₃CH₃ | C₂H₅ | Cl |
| Cl | H | H | N(C₂H₅)₂ | C₂H₅ | I |

A process has also been found for the preparation of 1H-pyrido-[2,3-b][1,4]-thiazines, wherein pyridine compounds of the formula

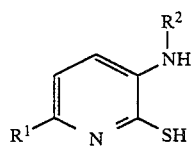
(III)

in which
R¹ denotes hydrogen, halogen, optionally substituted alkyl or alkoxy or the group

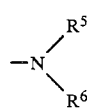

in which
R⁵ and R⁶ are identical or different and denote hydrogen, optionally substituted alkyl or aryl, or can be linked to form a 5- or 6-membered heterocyclic ring, and
R² denotes hydrogen or optionally substituted alkyl or alkoxy, are reacted with carbonyl compounds of the formula

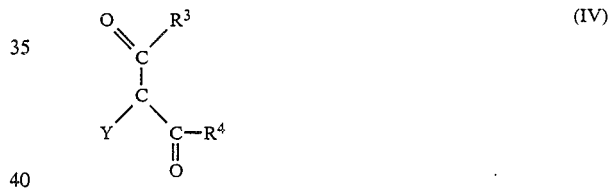
(IV)

in which
Y represents halogen,
R³ denotes hydrogen or optionally substituted alkyl or alkoxy and
R⁴ denotes hydroxyl, optionally substituted alkoxy or the group $$-N\begin{matrix}R^5\\R^6\end{matrix}$$

in which
R⁵ and R⁶ have the abovementioned meaning, wherein
R³ and R⁴ can be linked via a polymethylene chain to form a 5- to 7-membered carbocyclic ring, in the presence of a base and if appropriate in the presence of solvents.

The process according to the invention can be represented, for example, by the following equation:

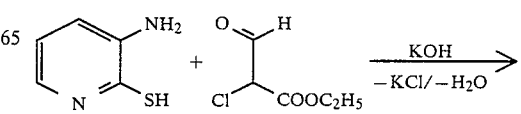

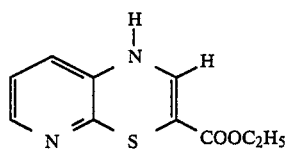

(V) 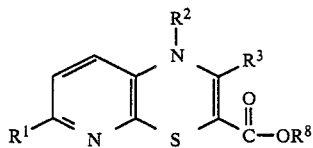

The pyridine compounds for the process according to the invention are known per se and can be prepared by known processes (Pyridine and its Derivatives, Part IV, 345-437, in The Chemistry of Heterocyclic Compounds, Editor: E. Klingsberg, John Wiley, New York—London Sydney, 1964; C.O. Okafor, Int. J. Sulfur Chem. B, 7, 121153 (1972) and C.O. Okafor, J. Org. Chem. 38, 4383 (1973)).

The carbonyl compounds for the process according to the invention are likewise known and can be prepared by known methods (K.H. Dudley et al., J. Heterocyclic Chem. 10, 938 (1973); Org. Synth. 21, 4, (1941) and C. Bülow and E. King, Liebigs Ann. Chem. 439, 211 (1924)).

Nucleofugic groups can be, for example, halogen (fluorine, chlorine, bromine or iodine) and 0-tosyl.

Since hydrogen halide is liberated in the reaction, it is advantageous to carry out the reaction in the presence of bases. Possible bases for this are inorganic bases, such as alkali metal or alkaline earth metal hydroxides or carbonates or the corresponding ammonium compounds, and organic bases, such as triethylamine or pyridine.

All the inert organic solvents can be employed as diluents. These include, preferably, ethers, such as dioxane and tetrahydrofuran, alcohols, such as methanol, ethanol or isopropanol, dipolar aprotic solvents, such as dimethylformamide, dimethyl sulphoxide or N-methylpyrrolidone, and water.

The process according to the invention can be carried out in the presence of exclusively one or several organic solvents or water and one or several waterimmiscible solvents.

The reaction temperatures can be varied within a substantial range. The reaction is in general carried out between about $-10°$ C. and about $+100°$ C., preferably between $0°$ C. and $+60°$ C. The reaction can be carried out under normal pressure, but also under reduced or increased pressure. It is in general carried out under normal pressure.

In carrying out the process according to the invention, it may be advantageous to work under an inert gas atmosphere, preferably under nitrogen. The pyridine compounds, carbonyl compounds and bases are preferably reacted in a molar ratio of 1:1:1 for the preparation of the compounds according to the invention.

Working up of the reaction mixtures for isolation of the compounds according to the invention is carried out in all cases in a generally known manner.

Variants A and B may be mentioned as particular embodiments in the context of the present invention:

Variant A

By this process, acid amines of 1H-pyrido-[2,3-b]-[1,4]-thiazines can preferably be prepared according to the invention by a procedure in which esters of the 1Hpyrido-[2,3-b][1,4]-thiazines of the formula in which $R^1$ denotes hydrogen, halogen, optionally substituted alkyl or alkoxy or the group

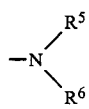

in which $R^5$ and $R^6$ are identical or different and denote hydrogen or optionally substituted alkyl or aryl, or can be linked to form a 5- or 6-membered heterocyclic ring, $R^2$ and $R^3$ are identical or different and denote hydrogen or optionally substituted alkyl or alkoxy and $R^8$ represents alkyl, are reacted with amines of the formula

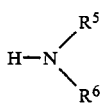

(VI)

in which $R^5$ and $R^6$ have the abovementioned meaning.

If, for example, 3-methoxycarbonyl-1H-pyrido-[2,3-b][1,4]-thiazine and aminoethanol are used as starting substances, the course of the reaction can be represented by the following equation:

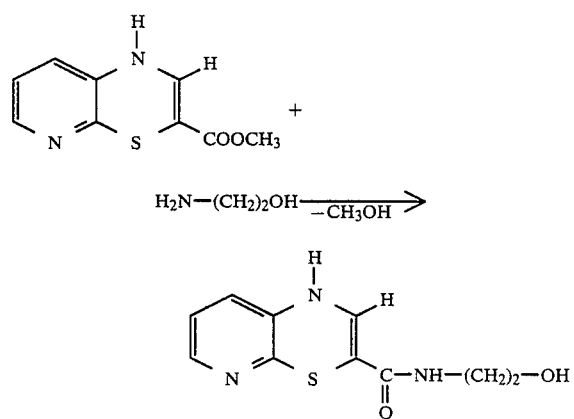

The esters of the formula (V) which can be used according to the invention can be prepared according to the invention, as described above, by reaction of the pyridine compounds of the formula (III) with carbonyl compounds of the formula (IV).

The amines for the process according to the invention are known (Houben Weyl, Volume 11/1, pages 9 to 1026, 1957). Possible diluents are all the inert organic solvents.

These include, preferably, chlorinated hydrocarbons, such as methylene chloride, chloroform, carbon tetrachloride, 1,2-dichloroethane, 1,2,2-trichloroethane and chlorobenzene, alcohols, preferably methanol, ethanol or isopropanol, ethers, such as dioxane or tetrahydrofuran, and dipolar aprotic solvents, such as dimethylformamide, dimethyl sulphoxide or N-methylpyrrolidone.

The process according to the invention can be carried out in the presence of exclusively one or several organic solvents.

A procedure in which the amine according to the invention, if it is liquid, is employed not only as the reagent but also as the solvent is particularly preferred.

The reaction temperatures can be varied within a substantial range. The reaction is in general carried out between about 0° C. and about 100° C., preferably between 0° C. and +60° C. The reaction can be carried out under normal pressure, but also under reduced or increased pressure. It is in general carried out under normal pressure.

The starting substances can be employed in equimolar amounts for carrying out the process according to the invention, but the use of an excess of amine is advantageous.

The working up of the reaction mixtures for isolation of the compounds according to the invention is carried out in all cases in the generally known manner. Variant B By this process, 1H-pyrido-[2,3-b][1,4]-thiazines preferably substituted in the 1-position can be prepared by a procedure in which 1H-pyrido-[2,3-b][1,4]-thiazines of the formula

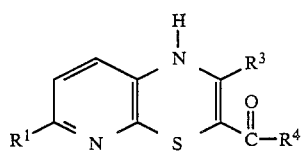

in which

R¹ denotes hydrogen, halogen, optionally substituted alkyl or alkoxy or the group

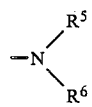

in which

R⁵ and R⁶ are identical or different and denote hydrogen, optionally substituted alkyl or aryl, or can be linked to form a 5- or 6-membered heterocyclic ring, R³ denotes hydrogen or optionally substituted alkyl or alkoxy and R⁴ denotes hydroxyl, optionally substituted alkoxy or the group

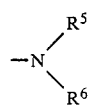

in which

R⁵ and R⁶ have the abovementioned meaning, wherein

R³ and R⁴ can be linked via a polymethylene chain to form a 5- to 7-membered carbocyclic ring, are reacted with halides or tosylates of the formula

R²—Z     (VIII)

in which

Z denotes halogen or 0-tosyl and

R² denotes optionally substituted alkyl or alkoxy, in the presence of bases.

If, for example, 3-ethoxycarbonyl-1H-pyrido-[2,3-b][1,4]-thiazine and ethyl bromoacetate are used as starting materials, the course of the reaction can be represented by the following equation:

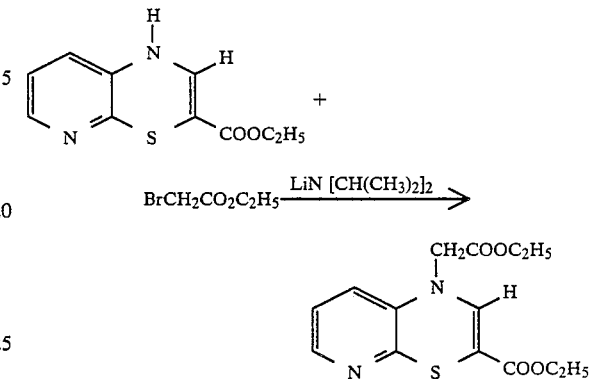

The 1H-pyrido-[2,3-b][1,4]-thiazines unsubstituted in the 1-position can be prepared according to the invention, as described above, by reaction of the pyridine compounds of the formula (III) with carbonyl compounds of the formula (IV).

The halides or tosylates are known (S.R. Sandler and W. Karo, Organic Functional Group Preparations Volume I, pages 148–179, Academic Press (1983)).

Possible diluents are inert organic solvents.

These include, preferably, ethers, such as dioxane, tetrahydrofuran and mono- or diglyme, and dipolar aprotic solvents, such as dimethylformamide, hexamethylphosphoric acid triamide or N-methylpyrrolidone.

The process according to the invention can be carried out in the presence of exclusively one or several organic solvents.

Examples of possible bases which can be used according to the invention are sodium hydride, organometallic reagents, such as butyllithium, phenyllithium, lithium diisopropylamide and Grignard compounds, such as methylmagnesium iodide, and alkali metal alcoholates, such as potassium tert.-butylate.

The reaction temperatures can be varied within a substantial range. The reaction is in general carried out between about −100° C. and about +100° C., preferably between −70° C. and +50° C. The reaction can be carried out under normal pressure, but also under reduced or increased pressure. It is in general carried out under normal pressure.

The starting substances can be employed in equimolar amounts in carrying out the process according to the invention, and the use of an excess of halide or tosylate and of the base may be advantageous.

The working up of the reaction mixtures for isolation of the compounds according to the invention is carried out in all cases in the generally known manner.

The preparation of the quaternary salts of the 1H-pyrido-[2,3-b][1,4]-thiazines can be represented, for example, by the following equation:

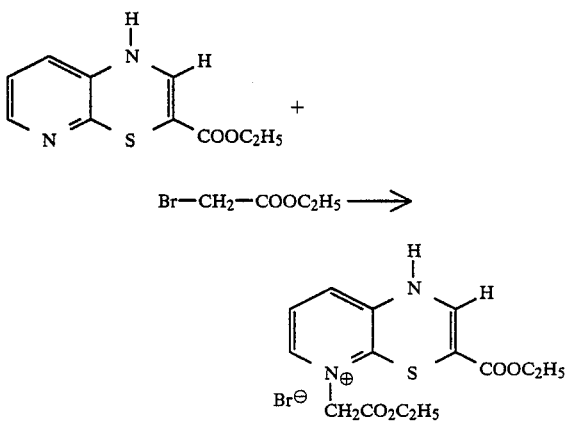

The quaternization is preferably carried out with alkyl halides or tosylates. The alkyl halides or tosylates are known (S.R. Sandler and W. Karo, Organic Functional Group Preparations, Volume I, pages 148–179, Academic Press (1983)).

Possible diluents are all the inert organic solvents. These include, preferably, solvents with a high dipole moment, such as nitromethane, nitrobenzene or acetonitrile. Other solvents which are likewise suitable are to be found in Houben-Weyl, Volume 11/2, page 596.

The process according to the invention can be carried out in the presence of exclusively one or several solvents.

The reaction temperatures can be varied within a substantial range. The reaction is in general carried out between about 0° C. and about +200° C., preferably between +20° C. and +200° C. The reaction can be carried out under normal pressure, but also under reduced or increased pressure. It is in general carried out under normal pressure.

The reaction partners can be employed in an equimolar ratio in carring out the process according to the invention, but it may be advantageous to use one component in excess.

The working up of the reaction mixture for isolation of the compounds according to the invention is carried out in all cases in the generally known manner. Replacement of the anions is likewise carried out in the generally known manner.

The quaternary salts can be represented by the formula

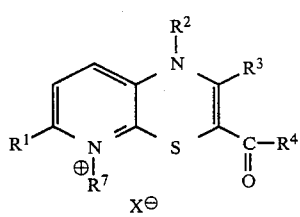

in which
$R^1$ to $R^4$, $R^7$ and X have the abovementioned meaning.

The 1H-pyrido-[2,3-b][1,4]-thiazines according to the invention are active compounds for medicaments and are suitable for the therapeutic treatment of humans and animals. They are lipoxygenase inhibitors and are particularly suitable for the treatment of inflammatory, allergic and asthmatic illnesses.

The new active compounds can be converted in a known manner into the customary formulations, such as tablets, capsules, dragees, pills, granules, aerosols, syrups, emulsions, suspensions and solutions, using inert, non-toxic pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case where water is used as a diluent, organic solvents can be used, if appropriate, as auxiliary solvents.

Examples of auxiliaries which may be mentioned are: water, non-toxic organic solvents, such as paraffins (for example petroleum fractions), vegetable oils (for example groundnut/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silicic acid and silicates), sugars (for example sucrose, lactose and glucose), emulsifying agents, such as non-ionic anionic emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, in particular perlingually or intravenously. In the case of oral use, tablets can of course also contain, in addition to the excipients mentioned, additives such as sodium citrate, calcium carbonate and dicalcium phosphate, together with various adjuvants, such as starch, preferably potato starch, gelatine and the like. Lubricants, such as magnesium stearate, sodium laury-sulphate and talc can furthermore be co-used for tablet-making. In the case of aqueous suspensions and/or elixirs intended for oral use, various flavour improvers or colorants can be added to the active compounds, in addition to the abovementioned auxiliaries.

In the case of parenteral use, solutions of the active compounds can be employed, using suitable liquid excipients.

In general, it has proved advantageous, in the case of intravenous administration, to administer amounts of about 0.01 to 10 mg/kg, preferably about 0.05 to 5 mg/kg of body weight per day in order to achieve effective results, and in the case of oral administration the dosage is about 0.05 to 100 mg/kg, preferably 0.1 to 10 mg/kg of body weight per day.

Nevertheless, it may at times be necessary to deviate from the amounts mentioned, and in particular to do so as a function of the body weight of the test animal or of the nature of the administration route, but also on the basis of the species of animal and its individual behaviour towards the medicament or the nature of its formulation and the time or interval at which administration takes place. Thus, it can in some cases suffice to manage with less than the abovementioned minimum amount, whilst in other cases the upper limit mentioned must be exceeded. Where relatively large amounts are administered, it may be advisable to divide these into several individual doses over the course of the day. The same dosage range is envisaged for administration in human medicine. The above statements also apply here in the general sense.

EXAMPLE 1

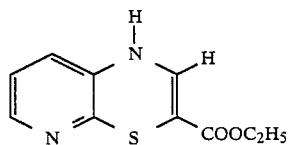

3-Ethoxycarbonyl-1H-pyrido[2,3-b][1,4]-thiazine 4.8 g of ethyl α-chloro-formylacetate, dissolved in 70 ml of ethanol, are added to a solution of 4 g (0.0317 mole) of 2-mercapto-3-aminopyridine and 1.78 g (0.0317 mole) of potassium hydroxide in 200 ml of ethanol at 25° C. under nitrogen. The mixture is warmed at 50° C. for 1 hour, the ethanol is then stripped off in vacuo and the residue is chromatographed on silica gel with methylene chloride/methanol (95:5) as the mobile phase. Yield: 3.3 g (47% of theory) Melting point: 194°–195° C.

| Example No. | The following compounds were prepared analogously: Formula | Melting point °C. | Yield % of theory |
|---|---|---|---|
| 2 | [structure with COOCH₃] | 199–201 | 86 |
| 3 | [structure with COOCH(CH₃)₂] | 172–174 | 34 |
| 4 | [structure with COO(CH₂)₃CH₃] | 156–158 | 45 |
| 5 | [structure with CONH-phenyl] | 193–198 | 68 |
| 6 | [structure with CH₃ and CONHC(CH₃)₃] | 118–121 | 52 |
| 7 | [structure with CH₃ and CON(CH₃)₂] | 170–173 | 15 |
| 8 | [structure with N-CH₃ and COOC₂H₅] | 113–115 | 63 |

-continued

The following compounds were prepared analogously:

| Example No. | Formula | Melting point °C. | Yield % of theory |
|---|---|---|---|
| 9 | 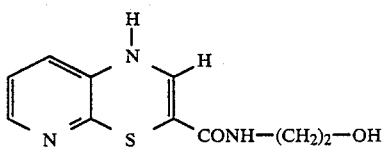 | 265–268 | 71 |

EXAMPLE 10

3-[(2-Hydroxyethylamino)carbonyl]-1H-pyrido[2,3-b][1,4]-thiazine 0.52 g (0.0025 mole) of 3-methoxycarbonyl-1Hpyrido[2,3]b][1,4]-thiazine are treated with 5 ml of aminoethanol at 25° C. for 25 hours. Thereafter, the excess reagent is distilled off in vacuo and the residue is chromatographed on silica gel, mobile phase: methylene chloride/methanol (86:14). Yield: 0.5 g (84% of theory) Melting point: 192°–195° C.

The following compounds were prepared analogously:

3.31 g (0.0185 mole) of ethyl bromoacetate are added to a solution of 0.5 g (0.00225 mole) of 3-ethoxy-carbonyl-1H-pyrido-[2,3-b][1,4]-thiazine in 10 ml of nitromethane and the reaction mixture is heated under reflux for 1 hour. It is then cooled to 25° C. and diethyl ether is added until crystallization starts. The crystals which precipitate when the mixture is left to stand are filtered off with suction and dried.

Yield: 0.35 g (40% of theory)
Melting point: 158°–159° C.

The following compounds were prepared analogously:

| Example No. | Formula | Melting point °C. | Yield % of theory |
|---|---|---|---|
| 15 | 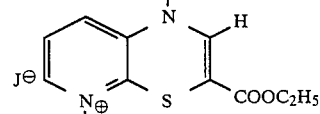 | 195–198 | 37 |

| Example No. | Formula | Melting point °C. | Yield % |
|---|---|---|---|
| 11 | ![structure] CONH(CH2)2N(C2H5)2 | 181–186 | 82 |
| 12 | ![structure] CONH—(CH2)3—N(CH3)2 | >160 (decomposition) | 92 |
| 13 | ![structure] CONH(CH2)2—NH2 | 130–137 | 50 |

EXAMPLE 14

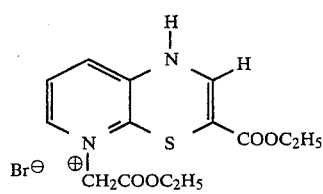

| 16 | ![structure] COOC2H5 with J⊖ N⊕ CH2CH3 | 142–152 | 49 |

EXAMPLE 17

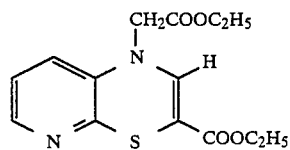

2.02 ml of 1.6 molar solution of n-butyllithium in n-hexane (0.00321 mole) are added to a solution, cooled to −20° C., of 0.36 g (0.00351 mole) of diisopropylamine in 10 ml of THF while stirring, under nitrogen and with exclusion of moisture. The mixture is stirred for 10 minutes and cooled to -70° C. and a solution of 0.5 g (0.00225 mole) of 3-ethoxycarbonyl-1H-pyrido[2,3-b][1,4]-thiazine in 10 ml of tetrahydrofuran is added dropwise. After addition of 0.5 g of hexamethylphosphoric acid triamide, the temperature of the reaction mixture is allowed to rise again to −20° C. and a solution of 0.63 g (0.00351 mole) of ethyl bromoacetate in 5 ml of tetrahydrofuran is added dropwise. The mixture is stirred at 25° C. until the conversion is complete. Thereafter, it is diluted with 200 ml of methylene chloride and extracted by shaking with 4 portions of 50 ml of water and the organic phase is dried over anhydrous sodium sulphate and concentrated. The residue is chromatographed on silica gel, mobile phase methylene chloride/methanol (97:3).

Yield: 0.54 g (78% of theory)
Melting point: 152°–155° C.

The following compounds were prepared analogously:

| Example No. | Formula | Melting point °C. | Yield % of theory |
|---|---|---|---|
| 18 | CH₃ ... COOC₂H₅ | 112–115 | 67 |
| 19 | CH₂—C≡N ... COOC₂H₅ | 157–158 | 72 |

USE EXAMPLES

Example 20

The lipoxygenase-inhibiting properties of the 1H-pyrido[2,3-b][1,4]-thiazines is demonstrated by methods analogous to those of Borgeat, P. Samuelsson, B. (1979), Proc. Nat. Acad. Sci. 76, 2148–2152 and Hamilton, J. G., Karol, R.J. (1982), Prog. Lipid Res. 21, 155–170.

Polymorphonuclear leucocytes from rats (PMNL) were obtained from the peritoneal space in Wistar rats 18 hours after intraperitoneal administration of 6 ml of a 12% strength sodium caseinate suspension.

The release of $LTB_4$ on polymorphonuclear granulocytes after addition of substances and calcium ionophor was determined by means of HPLC as a measure of the lipoxygenase inhibition.

After the PMNL had been centrifuged and washed with incubation buffer (137 mN NaCl; 2.7 mM KCl; 5.0 mM $Na_2HPO_4$; 5.55 mM glucose; and 2.0 mN $CaCl_2$ pH =7.2), the cell density was adjusted to $2 \times 10^7$ ml (Coulter counter) and 1 ml of this cell suspension was preincubated with 2.5 σl of dimethylsulphoxide of 2.5 σl of various test substance concentrations in dimethylsulphoxide at 37° C. for 5 minutes. After stimulation of the cells with 2.5 σl of calcium ionophor A 23187 (1 mg/ml of dimethylsulphoxide), the main incubation lasting 6 minutes was halted by addition of 1.5 ml of $PGB_2$-containing methanol (1 μl/ml), and 2 ml of cell-free supernatant were obtained by centrifugation (1,000 g, 3 minutes, room temperature) and, after acidification to pH 3.0 with 1 N HCl, were extracted twice with 4 ml of ether. The combined ether phases were washed with 4 ml of water (double distilled), dried while gassing with nitrogen and taken up in 80 μl of methanol.

20 μl of each of the samples thus prepared were applied to a pre-packed column (Nucleosil, type 7.5 C 18M 4×25 mm) and chromatographed at a flow rate of 1 ml/min (Kontron pump system 600), methanol, $H_2O$ and acetic acid (75:25:0.01) being used as the mobile phase. Detection was at 280 nm (Uvicon 720 LC). The formation of the metabolite was quantified with the aid of the internal standard PG $B_2$ as a quotient of the area integrals (Shimadzu C-R1B) of $LTB_4$ to $PGB_2$ and an inhibition was determined as a percentage of the controls. As can be seen from the following table, the 1H-pyrido-[2,3-b][1,4]-thiazines effect significant inhibition of $LTB_4$ biosynthesis in rat granulocytes.

Inhibition of leukotriene $B_4$ biosynthesis ($IC_{50}$)

| Compound from Example No. | | M/1 |
|---|---|---|
| 1 | | $4 \cdot 6 \cdot 10^{-7}$ |
| 2 | | $5 \cdot 10^{-6}$ |
| 4 | | $5 \cdot 5 \cdot 10^{-8}$ |
| 19 | | $2 \cdot 6 \cdot 10^{-6}$ |
|  | 42% at | $1 \cdot 10^{-5}$ |

The 1H-pyrido-[2,3-b][1,4]-thiazines according to the invention also have an in vivo action. This action is demonstrated by measurement of the inhibition of leucocyte migration by methods which are known per se (compare Higgs et al., Biochemical Pharmacology 28, 1959, (1979) and Eur. J. Pharmacol. 66, 81 (1980)).

The action of a 1H-pyrido-[2,3-b][1,4]-thiazine after local administration by insertion of a small sponge impregnated with active compound under the skin on the backs of rats may be mentioned as examples.

| Compound No. | Dose, Local (mg/rat) | Inhibition of Leucocyte migration (control = 0%) |
|---|---|---|
| 1 | 10 | 50 |

Example 21

The antiasthmatic action of the compounds according to the invention can likewise be demonstrated by methods which are already known (compared Samuelson et al., FEBS Letters, 110, 213 (1980) and Yen et al., Agents and Actions 10, 274 (1980)).

It will be understood that the specification and examples are illustrative but not limitative of the present invention and that other embodiments within the spirit and scope of the invention will suggest themselves to those skilled in the art.

What is claimed is:

1. A 1H-Pyrido-[2,3-b][1,4]-thiazine of the formula

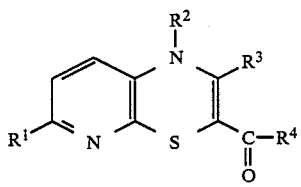

wherein
$R^1$ is hydrogen

$R^2$ and $R^3$ are identical or different and denote hydrogen, $C_1$ to $C_8$-alkoxy, $C_1$ to $C_8$-alkyl or $C_1$ to $C_8$-alkoxy or $C_1$ to $C_8$-alkyl substituted by halogen, hydroxyl, amino, dimethylamino, diethylamino, cyano, methoxycarbonyl or ethoxycarbonyl, $R^4$ denotes hydroxyl or

$C_1$ to $C_8$-alkoxy or $C_1$-$C_8$-alkoxy substituted by halogen, hydroxyl, amino, dimethylamino, diethylamino, cyano, methoxycarbonyl or ethoxycarbonyl, or $R^3$ and $R^4$ are linked via a polymethylene chain to form a 5 or 7-membered carbocyclic ring, and quaternary salts thereof.

2. A 1H-Pyrido-{2,3-b][1,4]thiazine according to claim 2,
wherein
$R^1$ is hydrogen,

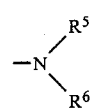

$R^2$ and $R^3$ are identical or different and are hydrogen or $C_1$-$C_6$-alkoxy, $C_1$-$C_6$-alkyl or $C_1$ to $C_6$-alkyl substituted by chlorine, bromine, hydroxyl, amino, dimethylamino, diethylamino, cyano, methoxycarbonyl or ethoxycarbonyl, $R^4$ is hydroxyl or

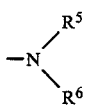

$C_1$ to $C_6$-alkoxy or $C_1$ to $C_6$-alkoxy substituted by chlorine, bromine, hydroxyl, amino, dimethylamino, diethylamino, cyano, methoxycarbonyl or ethoxycarbonyl, or $R^3$ and $R^4$ are linked via a polymethylene chain to form a 5 or 7-membered carbocyclic ring, and quaternary salts thereof.

3. A 1H-Pyrido-[2,3-b][1,4]-thiazine according to claim 1,
wherein
$R^1$ is hydrogen and $R^4$ is ethoxy having the formula

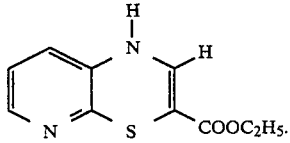

4. A 1H-Pyrido-[2,3-b][1,4]-thiazine according to claim 1,
wherein
$R^1$, $R^2$ and $R^3$ are hydrogen and $R^4$ is methoxy having the formula

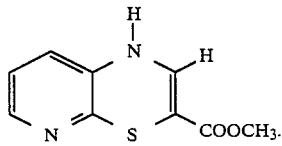

5. A 1H-Pyrido-[2,3-b][1,4]-thiazine according to claim 1,
wherein
$R^1$, $R^2$ and $R^3$ are hydrogen and $R^4$ is butoxy having the formula

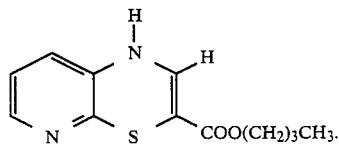

6. A 1H-Pyrido-[2,3-b][1,4]-thiazine according to claim 1,
wherein
$R^1$ and $R^3$ are hydrogen, $R^3$ is -CH$_2$-C=N and $R^4$ is ethoxy having the formula

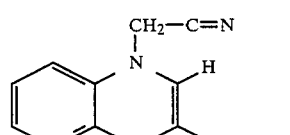

* * * * *

UNITED STATES PATENT AND TRADEMARK OFFICE
CERTIFICATE OF CORRECTION

PATENT NO. : 4,861,878
DATED : August 29, 1989
INVENTOR(S) : Gerd Fengler, et al It is certified that error appears in the above-identified patent and that said Letters Patent is hereby corrected as shown below:

| | |
|---|---|
| Title Page, under "Other Publications, line 10 | After "Institute)." insert --25.07,1975-- |
| Col. 2, line 38 and Col. 21, line 55 | Delete "{" and substitute --[-- |
| Col. 9, line 65 | Delete "amines" and substitute --amides-- |
| Col. 13, line 41 | Delete "carring" and substitute --carrying-- |
| Col. 17, line 28 | After "2,3" delete "]" |
| Col. 20, line 5 | After "$CaCl_2$" insert --,-- |
| Col. 21, lines 28-33; Col. 21, lines 41-45; Col. 21, lines 61-64 | Delete " $-N\begin{matrix}R^5\\R^6\end{matrix}$ " |
| Col. 21, line 56 | Delete "claim 2" and substitute --claim 1-- |

Signed and Sealed this

Eleventh Day of September, 1990

Attest:

HARRY F. MANBECK, JR.

Attesting Officer        Commissioner of Patents and Trademarks